(12) United States Patent
Kassab

(10) Patent No.: US 12,427,045 B2
(45) Date of Patent: Sep. 30, 2025

(54) EXPANDABLE ENDOGRAFT DEVICES, SYSTEMS, AND METHODS OF USING THE SAME TO PARTIALLY OR FULLY OCCLUDE A LUMINAL ORGAN

(71) Applicant: Ghassan S. Kassab, La Jolla, CA (US)

(72) Inventor: Ghassan S. Kassab, La Jolla, CA (US)

( * ) Notice: Subject to any disclaimer, the term of this patent is extended or adjusted under 35 U.S.C. 154(b) by 982 days.

(21) Appl. No.: 17/534,071

(22) Filed: Nov. 23, 2021

(65) Prior Publication Data

US 2022/0079787 A1    Mar. 17, 2022

Related U.S. Application Data

(63) Continuation of application No. 16/246,781, filed on Jan. 14, 2019, now Pat. No. 11,179,256.

(60) Provisional application No. 62/617,211, filed on Jan. 13, 2018.

(51) Int. Cl.
  *A61F 2/958*   (2013.01)
  *A61B 17/12*   (2006.01)
  *A61F 2/07*    (2013.01)
  *A61F 2/82*    (2013.01)

(52) U.S. Cl.
  CPC ............ *A61F 2/958* (2013.01); *A61B 17/12* (2013.01); *A61B 17/12031* (2013.01); *A61B 17/12036* (2013.01); *A61B 17/12109* (2013.01); *A61B 17/12136* (2013.01); *A61B 17/12168* (2013.01); *A61B 17/12186* (2013.01); *A61B 17/1219* (2013.01); *A61F 2/07* (2013.01); *A61F 2002/077* (2013.01); *A61F 2/82* (2013.01)

(58) Field of Classification Search
  CPC .... A61F 2/958; A61F 2/07; A61F 2/82; A61F 2002/077; A61F 2002/823; A61F 2250/0067; A61F 2/945; A61B 17/12; A61B 17/12031; A61B 17/12036; A61B 17/12109; A61B 17/12136; A61B 17/12168; A61B 17/12186; A61B 17/1219
  See application file for complete search history.

(56) References Cited

U.S. PATENT DOCUMENTS

| | | | | |
|---|---|---|---|---|
| 6,187,370 B1* | 2/2001 | Dinh | ......................... | A61F 2/88 264/28 |
| 9,358,140 B1* | 6/2016 | Connor | ...................... | A61F 2/91 |
| 2005/0033409 A1* | 2/2005 | Burke | ................. | A61B 17/1219 623/1.15 |
| 2010/0076401 A1* | 3/2010 | Von Oepen | .............. | A61F 2/958 604/509 |
| 2012/0004682 A1* | 1/2012 | Connor | ............ | A61B 17/12168 606/194 |
| 2013/0150661 A1* | 6/2013 | Rosen | ................... | A61F 2/0022 600/29 |
| 2013/0190857 A1* | 7/2013 | Mitra | ....................... | A61L 31/06 623/1.36 |
| 2017/0014248 A1* | 1/2017 | Kelly | ........................ | A61F 2/86 |

* cited by examiner

*Primary Examiner* — Andrew Restaino

(57) ABSTRACT

Expandable endograft devices, systems, and methods of using the same to partially or fully occlude a luminal organ. An endograft device described herein may include a stent portion and a wall portion, wherein the wall portion is configured to receive a substance therein.

17 Claims, 4 Drawing Sheets

EXPANDABLE ENDOGRAFT DEVICES, SYSTEMS, AND METHODS OF USING THE SAME TO PARTIALLY OR FULLY OCCLUDE A LUMINAL ORGAN

PRIORITY

The present U.S. Nonprovisional patent application is related to, claims the priority benefit of, and is a U.S. continuation application of, U.S. patent application Ser. No. 16/246,781, filed on Jan. 14, 2019 and issued as U.S. Pat. No. 11,179,256 on Nov. 23, 2021, which is related to, and claims the priority benefit of, U.S. Provisional Patent Application Ser. No. 62/617,211, filed on Jan. 13, 2018, the contents of which are hereby incorporated by reference in their entirety into this disclosure.

BACKGROUND

Various stents and endografts are currently available in the medical marketplace for use with various medical procedures, including those procedures involving stent or endograft placement within an artery. However, in various situations, the medical practitioner may wish to also partially or fully occlude the luminal organ during or after the procedure, and the options to accomplish the same with a percutaneous intravascular procedure are quite limited.

In view of the same, devices and systems, such as expandable endograft devices and systems, and methods of using the same to partially or fully occlude a luminal organ, would be well appreciated in the medical arts.

BRIEF SUMMARY

The present disclosure includes disclosure of endograft devices, as shown and/or described.

The present disclosure includes disclosure of an endograft device, comprising a stent portion and a wall portion, wherein the wall portion is configured to receive a substance therein.

The present disclosure includes disclosure of an endograft device, wherein the wall portion surrounds all of the stent portion.

The present disclosure includes disclosure of an endograft device, wherein the wall portion surrounds part of the stent portion.

The present disclosure includes disclosure of an endograft device, wherein the wall portion extends an entire length of the endograft device/the stent portion.

The present disclosure includes disclosure of an endograft device, wherein the wall portion does not surround any part of the stent portion.

The present disclosure includes disclosure of an endograft device, wherein the wall portion is configured to attach to a delivery tube so that a substance can be delivered from a delivery apparatus, through the delivery tube, and into the wall portion, to partially or fully occlude a lumen of the endograft device.

The present disclosure includes disclosure of endograft systems, as shown and/or described.

The present disclosure includes disclosure of an endograft system, comprising an endograft device and at least one other item, such as a delivery tube and a delivery apparatus.

The present disclosure includes disclosure of a method of using an endograft device, as shown and/or described.

The present disclosure includes disclosure of a method of using an endograft system, as shown and/or described.

The present disclosure includes disclosure of an endograft device, comprising a stent portion, a wall portion, and wherein the wall portion is configured to receive a substance therein.

The present disclosure includes disclosure of an endograft device, wherein the wall portion surrounds all of the stent portion.

The present disclosure includes disclosure of an endograft device, wherein the wall portion surrounds part of the stent portion.

The present disclosure includes disclosure of an endograft device, wherein the wall portion extends an entire length of the endograft device or the stent portion.

The present disclosure includes disclosure of an endograft device, wherein the wall portion does not surround any part of the stent portion.

The present disclosure includes disclosure of an endograft device, wherein the wall portion is configured to attach to a delivery tube so that a substance can be delivered from a delivery apparatus, through the delivery tube, and into the wall portion, to partially or fully occlude a lumen of the endograft device.

The present disclosure includes disclosure of an endograft device, comprising a stent portion and an expandable wall portion positioned on the stent portion.

The present disclosure includes disclosure of an endograft device, wherein the wall portion is generally positioned within a lumen defined within the endograft device.

The present disclosure includes disclosure of an endograft device, wherein the wall portion is also positioned external of the endograft device.

The present disclosure includes disclosure of an endograft device, wherein the wall portion comprises a substance therein.

The present disclosure includes disclosure of an endograft device, wherein the wall portion further comprises a fluid permeable material.

The present disclosure includes disclosure of an endograft device, wherein the substance comprises ameroid particles.

The present disclosure includes disclosure of an endograft device, wherein the fluid permeable material prevents the substance from escaping the wall portion.

The present disclosure includes disclosure of an endograft device, wherein the wall portion is expandable to at least partially occlude a lumen of a luminal organ.

The present disclosure includes disclosure of an endograft device, further comprising an inner balloon, the inner balloon comprising a reactive material, wherein the reactive material reacts with available materials within a mammalian body to expand the wall portion.

The present disclosure includes disclosure of an endograft device, wherein the reactive material comprises glucose.

The present disclosure includes disclosure of an endograft device, wherein the available material within the mammalian body comprises oxygen.

The present disclosure includes disclosure of a method of using an endograft device, comprising the steps of positioning an endograft device into a luminal organ, the endograft device comprising a stent portion and an expandable wall portion positioned on the stent portion; expanding said endograft device within the luminal organ; and injecting a substance into the wall portion.

The present disclosure includes disclosure of a method of using an endograft device, further comprising the step of reacting the substance with materials available within a mammalian body so that the wall portion expands to occlude the luminal organ.

The present disclosure includes disclosure of a method of using an endograft device, wherein the step of injecting a substance into the wall portion is accomplished by delivery of the substance from a delivery apparatus and through a delivery tube attached to the wall portion.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein.

Figure 1:
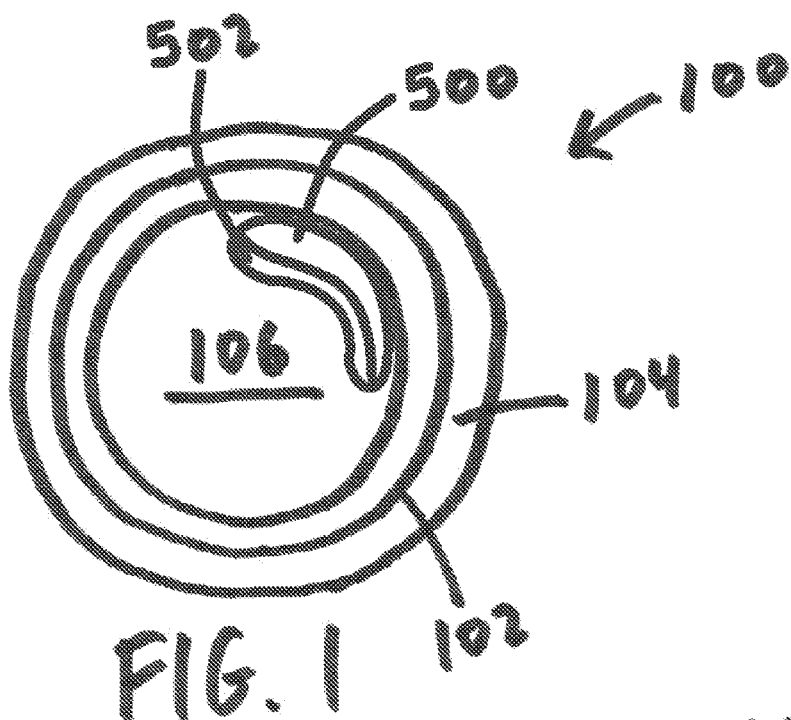
FIG. 1 shows an end view of an endograft device having a wall portion fully surrounding a stent portion, according to an exemplary embodiment of the present disclosure.

As such, an overview of the features, functions and/or configurations of the components depicted in the various figures will now be presented. It should be appreciated that not all of the features of the components of the figures are necessarily described and some of these non-discussed features (as well as discussed features) are inherent from the figures themselves. Other non-discussed features may be inherent in component geometry and/or configuration. Furthermore, wherever feasible and convenient, like reference numerals are used in the figures and the description to refer to the same or like parts or steps. The figures are in a simplified form and not to precise scale.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Figure 2:
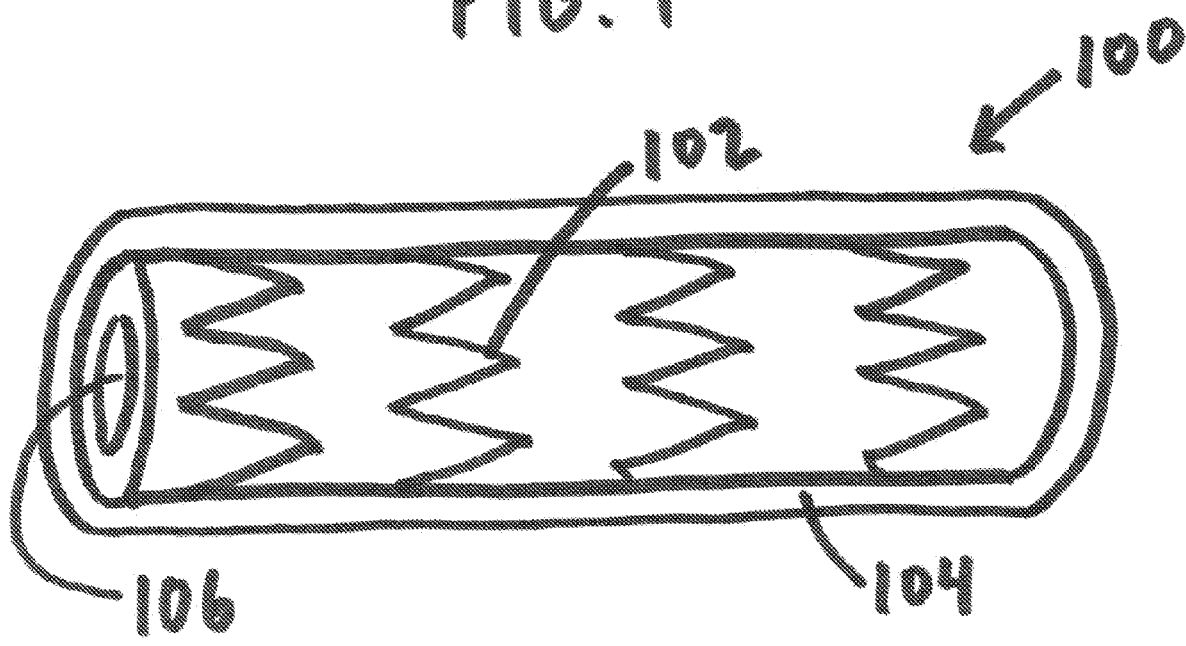
FIG. 2 shows side/perspective view of an endograft device having a wall portion fully surrounding a stent portion, according to an exemplary embodiment of the present disclosure.

An exemplary endograft device of the present disclosure is shown in FIG. 1 (end view) and FIG. 2 (side/perspective view). As shown therein, endograft device 100 comprises a stent portion 102 (such as a traditional metal, non-metal, or metal/non-metal hybrid stent) coupled to an expandable wall portion 104. As with a traditional endograft, stent portion 102 is configured to expand within a luminal organ, such as a blood vessel or other luminal organ, upon placement therein.

Figure 3:
FIG. 3 shows an end view of an endograft device having a wall portion partially surrounding a stent portion, according to an exemplary embodiment of the present disclosure.
Figure 4:
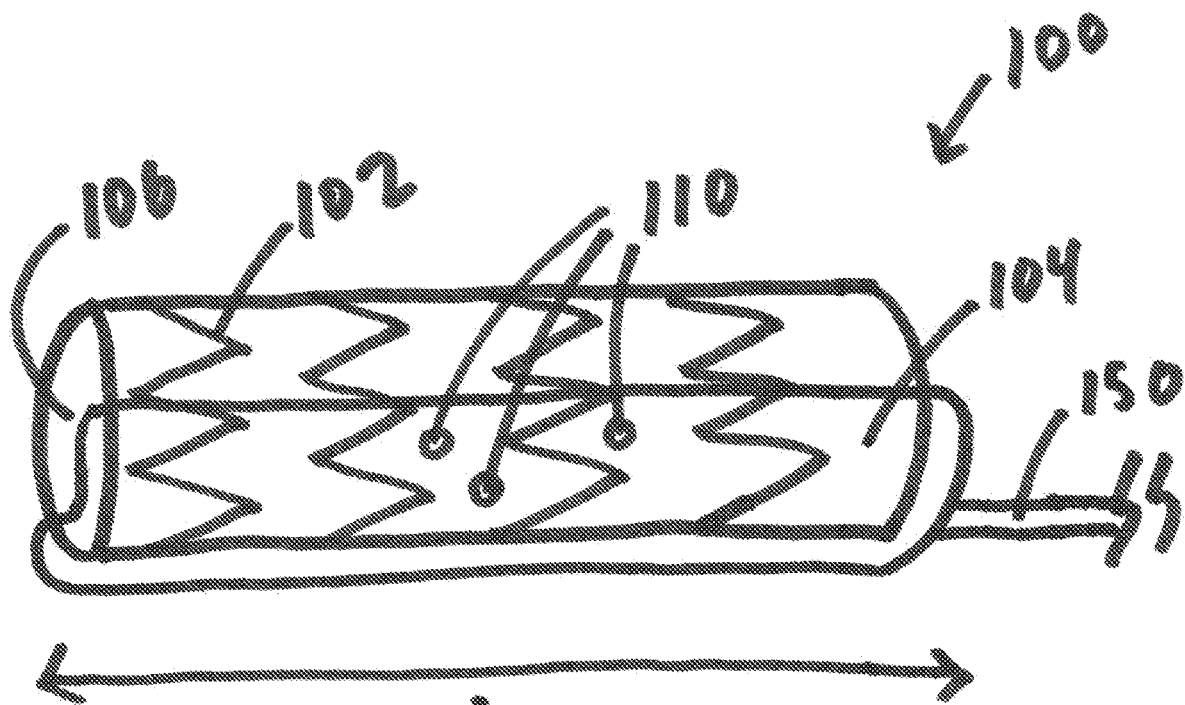
FIG. 4 shows side/perspective view of an endograft device having a wall portion partially surrounding a stent portion, according to an exemplary embodiment of the present disclosure.
Figure 5:
FIG. 5 shows an end view of an endograft device having a wall portion generally inside a stent portion, according to an exemplary embodiment of the present disclosure.
Figure 6:
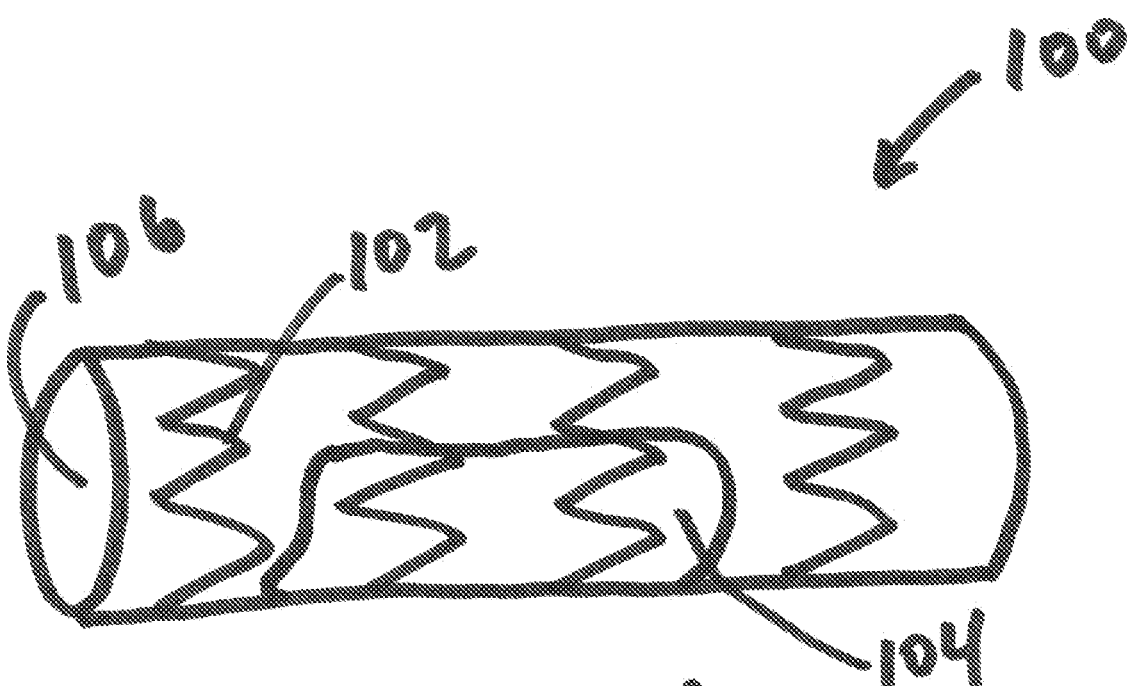
FIG. 6 shows side/perspective view of an endograft device having a wall portion generally inside a stent portion, according to an exemplary embodiment of the present disclosure.

Expandable wall portion 104, as shown in FIGS. 1 and 2, can surround all of stent portion 102, in at least some embodiments. In other embodiments, such as shown in FIGS. 3 and 4, wall portion 104 can surround less than part (some) of stent portion 102. Wall portion 104, in some embodiments and as shown in FIG. 4, can extend an entire length (L) of the endograft device 100/stent portion 102, and in other embodiments, such as shown in FIG. 6, wall portion can extend less than an entire length (L) of the endograft device 100/stent portion 102, such as part of said length (L). FIGS. 5 and 6 show an exemplary endograft device embodiment 100 whereby wall portion 104 does not surround any of stent portion 102, but instead is generally positioned within a lumen 106 defined within endograft device 100.

Figure 7:
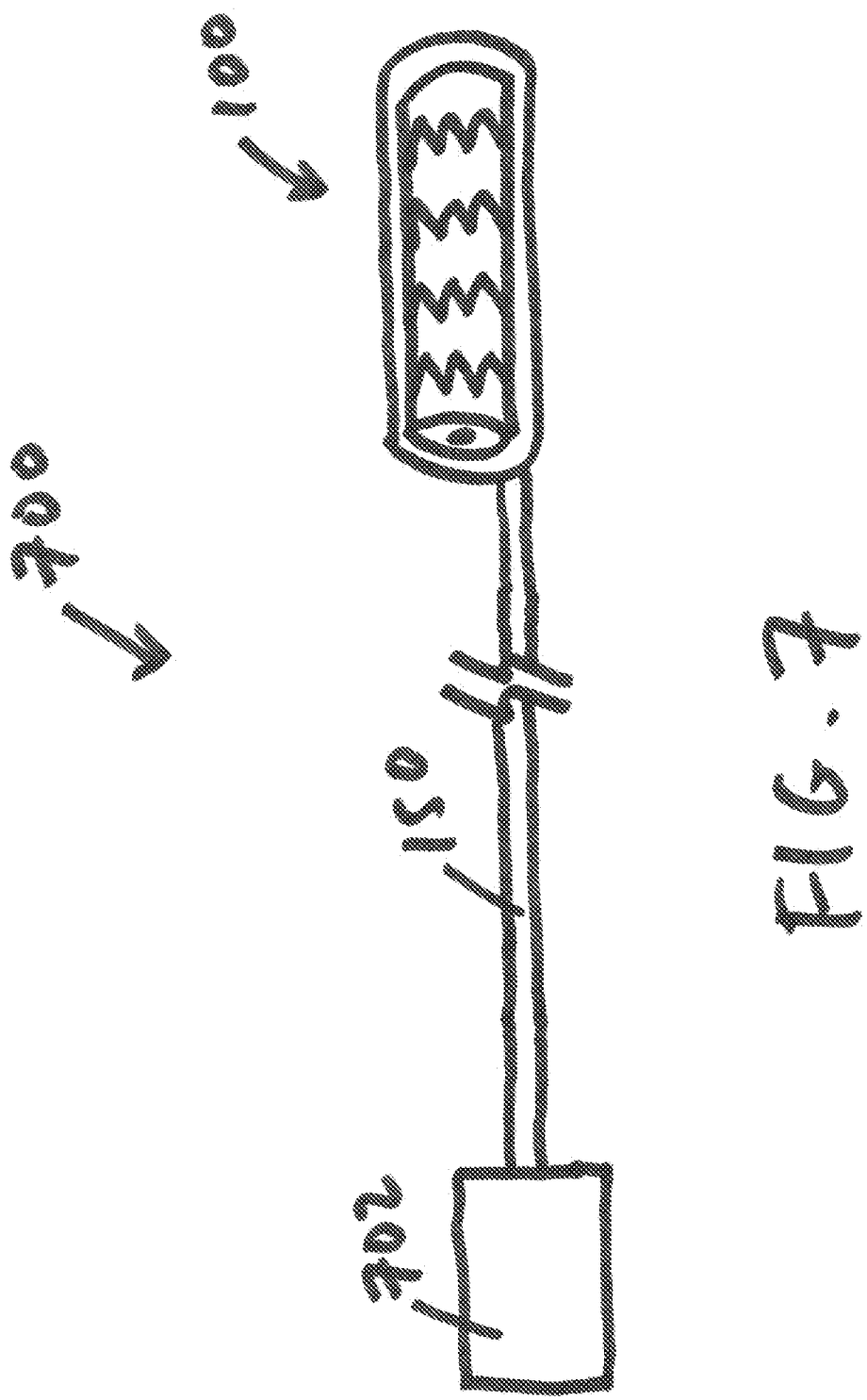
FIG. 7 shows a component diagram of a system comprising an endograft device and other components, according to an exemplary embodiment of the present disclosure.

Wall portions 104 of the present disclosure, as referenced herein, are configured to receive a substance 110 therein, such as relatively small ameroid particles, other particles (such as dehydrated proteins), by way of a delivery tube 150 connected to wall portion 104, such as shown in FIG. 4 for example. FIG. 7 shows elements of an exemplary system 700 of the present disclosure, comprising an exemplary endograft device 100 of the present disclosure, a delivery tube 150, and a delivery apparatus 702 (such as a syringe or other delivery apparatus) configured to deliver substance 110 through delivery tube 150 and into wall portion 104 of endograft device 100.

Slow chemical reactions that can produce a gas (such as carbon dioxide) can be used to expand the expandable wall portion 104 of the endograft device 100 to constrict the lumen 106, such as aerobic respiration. An inner balloon 500, for example and such as shown in FIG. 1, could have a reactive material 502 therein, such as glucose (whereby inner balloon 500 is lined with or otherwise contains glucose), and could react with oxygen absorbed from the blood vessel to produce carbon dioxide, water, and some heat. Expansion of inner balloon 500 due to said generated gas, such as when inner balloon is positioned within lumen 106 of endograft device, can cause expandable wall portion 104 to expand. Other chemical reactions can also be used, such as whereby a reactive material 502 within inner balloon 500 can react with available materials within the body (such as oxygen, as noted above), to generate a gas used to expand the balloon 500 and therefore the expandable wall portion 104 itself.

In at least one exemplary method of using an endograft device 100 or system 700 of the present disclosure, the method comprises the steps of positioning an exemplary endograft device 100 of the present disclosure into a mammalian luminal organ and expanding said endograft device 100 within the luminal organ. Methods of the present disclosure can then further comprise the steps of injecting a substance 110 into wall portion 104 of endograft device 100, such as to dilate the thickness of the endograft device 100, and hence occlude the lumen of the mammalian blood vessel to a desired degree during implantation of the endograft device 100 within the mammalian luminal organ. The substance 110 (such as ameroid particles or other dehydrated protein) can absorb fluid to swell the thickness of the endograft (namely to increase an overall size of wall portion 104, such as into or further into the lumen 106 of the endograft device 100) and hence further occlude the lumen of the luminal organ for additional or full closure. As such, exemplary wall portions 104 of the present disclosure comprise a fluid-permeable material, so to allow fluid from within the luminal organ to pass from the luminal organ, through the fluid-permeable material, and into the wall portion 104, whereby the combination of the fluid and the substance 110 causes substance 100 to swell (absorb the fluid). Such a fluid-permeable material would fully or at least substantially prevent substance 110 from within wall portions 104 from escaping wall portion 104. Such a device 100, system 700, and method is therefore novel as prior to the present disclosure, no said device 100 was configured as such, so to allow portions of the endograft device 100 to expand to occlude the lumen 106, as described herein, done percutaneously and intravascularly as desired. Said methods can be performed within a lumen of an artery (an exemplary luminal organ) and not external thereto, so that the entire procedure is performed intravascularly.

While various embodiments of endograft devices and systems and methods for using the same to partially or fully occlude a luminal organ have been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A method of using an endograft device, comprising the steps of:
   positioning the endograft device into a luminal organ, the endograft device comprising
      a stent portion,
      a wall portion configured to receive a substance therein, and
      an inner balloon, the inner balloon comprising a reactive material, wherein the reactive material is configured to react with available materials within a mammalian body to expand the wall portion, and wherein the reactive material comprises glucose;
   expanding said endograft device within the luminal organ; and
   injecting the substance into the wall portion.

2. The method of using the endograft device of claim 1, further comprising the step of:
   reacting the substance with the materials available within the mammalian body so that the wall portion expands to occlude the luminal organ.

3. The method of using the endograft device of claim 2, wherein the step of injecting the substance into the wall portion is accomplished by delivery of the substance from a delivery apparatus and through a delivery tube attached to the wall portion.

4. The method of using the endograft device of claim 1, wherein the wall portion surrounds all of the stent portion.

5. The method of using the endograft device of claim 1, wherein the wall portion extends an entire length of the endograft device or the stent portion.

6. The method of using the endograft device of claim 1, wherein the wall portion surrounds a part of the stent portion.

7. The method of using the endograft device of claim 1, wherein the wall portion does not surround any part of the stent portion.

8. A method of using an endograft device, comprising the steps of:
   positioning the endograft device into a luminal organ, the endograft device comprising
      a stent portion,
      an expandable wall portion positioned on the stent portion, and
      an inner balloon, the inner balloon comprising a reactive material, wherein the reactive material is configured to react with available materials within a mammalian body to expand the expandable wall portion, and wherein the reactive material comprises glucose; and
   expanding said endograft device within the luminal organ.

9. The method of using the endograft device of claim 8, wherein the expandable wall portion comprises a substance therein.

10. The method of using the endograft device of claim 8, wherein the expandable wall portion is generally positioned within a lumen defined within the endograft device.

11. The method of using the endograft device of claim 10, wherein the expandable wall portion is also positioned external of the endograft device.

12. The method of using the endograft device of claim 9, further comprising the step of:
   reacting the substance with the materials available within the mammalian body so that the expandable wall portion expands to occlude the luminal organ.

13. The method of using the endograft device of claim 12, wherein the expandable wall portion further comprises a fluid permeable material.

14. The method of using the endograft device of claim 13, wherein the substance comprises ameroid particles.

15. The method of using the endograft device of claim 13, wherein the fluid permeable material prevents the substance from escaping the expandable wall portion.

16. The method of using the endograft device of claim 8, wherein the expandable wall portion is expandable to at least partially occlude a lumen of the luminal organ.

17. The method of using the endograft device of claim 8, wherein the available materials within the mammalian body comprise oxygen.

* * * * *